United States Patent [19]
Klemp

[11] Patent Number: 5,498,279
[45] Date of Patent: Mar. 12, 1996

[54] HIGH SPEED GAS CHROMATOGRAPHY SYSTEM FOR ANALYSIS OF POLAR ORGANIC COMPOUNDS

[75] Inventor: Mark A. Klemp, Swartz Creek, Mich.

[73] Assignee: Chromatofast, Ann Arbor, Mich.

[21] Appl. No.: 242,348

[22] Filed: May 13, 1994

[51] Int. Cl.$^6$ .................................................. B01D 15/08
[52] U.S. Cl. ........................................... 96/104; 96/105
[58] Field of Search ................................. 96/101–107

[56] References Cited

U.S. PATENT DOCUMENTS

| | | | |
|---|---|---|---|
| 2,972,246 | 2/1961 | Reinecke et al. | 73/23 |
| 3,049,909 | 8/1962 | Thomas | 73/23 |
| 3,094,862 | 6/1963 | Burk | 73/23 |
| 3,111,835 | 11/1963 | Jenkins | 73/23 |
| 3,112,639 | 12/1963 | Maxwell | 73/23 |
| 3,119,251 | 1/1964 | Bowers | 73/23 |
| 3,159,019 | 12/1964 | DeFord | 73/23 |
| 3,201,971 | 8/1965 | Villalobos | 73/23.1 |
| 3,206,968 | 9/1965 | Leggoe et al. | 73/23.1 |
| 3,220,164 | 11/1965 | Golay | 73/23.42 X |
| 3,234,779 | 2/1966 | Dawson, Jr. | 96/104 X |
| 3,236,603 | 2/1966 | Durrett et al. | 96/103 X |
| 3,285,701 | 11/1966 | Robertson | 23/232 |
| 3,330,150 | 7/1967 | Loyd et al. | 73/23.1 |
| 3,422,665 | 1/1969 | Haase | 96/102 X |
| 3,435,659 | 4/1969 | Sternberg | 73/23.1 |
| 3,451,255 | 6/1969 | Neville et al. | 73/23.1 |
| 3,483,731 | 12/1969 | Sanford et al. | 73/23.1 |
| 3,511,080 | 5/1970 | Roof | 73/23.1 |
| 3,514,262 | 5/1970 | Ayers et al. | 23/230 |
| 3,518,059 | 6/1970 | Levy | 96/103 X |
| 3,550,428 | 12/1970 | Mator et al. | 73/23.36 |
| 3,650,090 | 3/1972 | Temple et al. | 55/31 |
| 3,653,840 | 4/1972 | Silas | 23/230 R |
| 3,712,028 | 1/1973 | Deans | 96/101 X |
| 3,807,217 | 4/1974 | Wilkins et al. | 73/23.1 |
| 4,007,626 | 2/1977 | Roof | 73/23.1 |
| 4,100,790 | 7/1978 | Harvey | 73/23.1 |
| 4,180,389 | 12/1979 | Paul | 96/101 X |
| 4,274,967 | 6/1981 | Snyder | 96/104 X |
| 4,302,422 | 11/1981 | Takahashi | 422/88 |
| 4,305,906 | 12/1981 | Mikasa et al. | 422/62 |
| 4,384,471 | 5/1983 | Wentzel | 73/23.1 |

(List continued on next page.)

FOREIGN PATENT DOCUMENTS 2823445  12/1979  Germany .................................. 96/104

OTHER PUBLICATIONS

*Sample Enrichment in High Speed Narrow Bore Capillary Gas Chromatography*, A. Van Es, J. Janssen, C. Cramers, and J. Rijks, Journal of High Ressolution Chromatography & Chromatography Communications, 1988, pp. 852–856.

*Rapid Evaporation of Condensed Gas Chromatographic Fractions*, J. Hopkins and Victor Pretorius, Journal of Chromatography, 1978, pp. 465–469.

*Electrically Heated Cold Trap Inlet System for High–Speed Gas Chromatography*, Ewels and Sacks, Analytical Chemistry, vol. 57, No. 14, Dec. 1985.

*Electrically Heated Cold Trap Inlet System for Computer–Controlled High–Speed Gas Chromatography*, Lanning, Sacks, Mouradian, Levine and Foulke, Analytical Chemistry, 1988, vol. 60, No. 18.

*High–Speed Gas Chromatography Using an On–Column Thermal Desorption Modulator*, Liu and Phillips, Dept. of chemistry and Biochemistry, Southern Illinois University, J Microcolumn Separations, vol. 1, No. 5, 1989.

Primary Examiner—Robert Spitzer
Attorney, Agent, or Firm—Harness, Dickey & Pierce

[57] ABSTRACT

Gas chromatography systems which provide for high speed separation of polar compounds of interest from samples which also include non-polar compounds. Efficient separation is achieved through the use of a tandem series connected combination of analytical columns, one of which having a polar stationary phase material and another having a non-polar stationary phase material. In two embodiments of the invention the order of the analytical columns is reversed. Fluid flow conduits, valves and vents are provided in a manner which eliminates mechanical valves in a sample stream.

17 Claims, 1 Drawing Sheet

U.S. PATENT DOCUMENTS

| | | | |
|---|---|---|---|
| 4,500,432 | 2/1985 | Poole et al. | 210/659 |
| 4,553,985 | 11/1985 | Dahlgren et al. | 55/67 |
| 4,923,486 | 5/1990 | Rubey | 55/67 |
| 5,028,243 | 7/1991 | Rubey | 55/67 |
| 5,057,126 | 10/1991 | Lubkowitz et al. | 55/67 |
| 5,096,471 | 3/1992 | Sacks et al. | 95/86 |
| 5,141,532 | 8/1992 | Sacks et al. | 96/102 X |
| 5,141,534 | 8/1992 | Sacks et al. | 96/102 |
| 5,205,845 | 4/1993 | Sacks et al. | 96/104 X |
| 5,281,256 | 1/1994 | Sacks et al. | 95/86 |
| 5,288,310 | 2/1994 | Peters et al. | 96/104 | ns of ct-

HIGH SPEED GAS CHROMATOGRAPHY SYSTEM FOR ANALYSIS OF POLAR ORGANIC COMPOUNDS

BACKGROUND AND SUMMARY OF THE INVENTION

This invention relates to a high speed gas chromatography system and particularly to such a system for improved rapid separation of polar compounds of an analyte mixture.

Gas chromatography (GC) is unsurpassed in its selectivity, sensitivity, and cost effectiveness. It is applicable for at least several hundred thousand compounds of low to moderate boiling point, including compounds in the $C_1$ to $C_5$ range. The process is also unique in its ability to obtain complete separation of complex mixtures of compounds.

In gas chromatography analysis the analyte mixture is separated into its components by eluting them from a column having a sorbent by means of a moving gas. In gas-liquid chromatography, which is a type in widespread use at present, the column comprises a nonvolatile liquid or solid sorbent coated as a thin layer on an inner support structure, generally the inside surface of a capillary tube. The moving gas phase, called the carrier gas, flows through the chromatography analytical column. The analyte partitions itself between the moving gas phase and the sorbent and moves through the column at a rate dependent upon the partition coefficients or solubilities of the analyte components. The analyte is introduced at the entrance end of the analytical column within the moving carrier gas stream. The components making up the analyte become separated along the column and elute at intervals characteristic of the properties of the analyte components. A detector, for example, a thermal conductivity detector or a flame ionization detector (FID) at the exit end of the analytical column responds to the presence of the analyte components. Upon combustion of the eluted components at the FID, charged species are formed in the flame. The flame characteristics are monitored through a biased ion detector which, along with associated signal processing equipment, produces a chromatogram which is a time versus detector signal output curve. The trace for complex mixtures includes numerous peaks of varying intensity. Since individual constituents of the analyte produce peaks at characteristic times and whose magnitude is a function of their concentration, much information is gained through an evaluation of a chromatogram.

While gas chromatography systems presently available perform satisfactorily, designers of such systems are continually attempting to optimize the capabilities of this separation procedure. Of particular interest is providing high speed gas chromatography for process stream control in industrial applications and in monitoring transient processes, for example, internal combustion engine exhaust gas compositions. The use of special inlet systems when combined with relatively short analytical columns operated at high carrier gas flow rates, has allowed separation of relatively simple mixtures on a time scale of a few seconds. However, some samples require much longer separation times because of the probability of co-eluting components. This probability is the result of the inevitable decrease in resolution when separation times are drastically reduced. To make high speed separation more practical, and to be able to apply fast gas chromatography techniques to a wider range of potential applications, it is necessary to enable adjustment of the selectivity of the system for specific sets of target compounds. Isolation of target compounds from other compounds minimizes potential chromatographic interferences and minimizes the separation time. By isolating the target compounds, the final separation step involves fewer compounds, and this can drastically reduce separation time.

In the analysis of some mixtures such as automotive exhausts and automotive fuels, chemical manufacturing process monitoring and the analysis of chlorinated hydrocarbon solvents in the environment, the particular compounds of interest are comprised of polar molecules. In many cases, other components of a sample such as so-called permanent gases, non-polar hydrocarbons and other classes of molecules are not of particular interest. Therefore, in some applications there is a need to quantify and separate only polar organic molecules. In conventional gas chromatography processes, other compounds such as non-polar organic molecules tend to co-elute with the target polar molecules of interest especially where the boiling points of the two groups of compounds are similar. The presence of co-elution renders it more difficult to separate the polar molecules since well defined chromatogram peaks are necessary for each molecule in the sample in order to successfully and accurately quantify it. As mentioned previously, the interests of obtaining rapid separation and definition and the ability to quantify sample constituents are conflicting. Accordingly, there is a need for a fast gas chromatography system for some applications in which target polar organic molecules can be rapidly separated from other types of molecules and separated to the degree that meaningful quantitive measurements can be obtained.

In accordance with this invention several embodiments of high speed gas chromatography system are described. Both embodiments utilize a tandem combination of analytical columns having polar and non-polar specific stationary phases. A combination of valves and pneumatic restrictors are used to isolate the polar compounds by means of venting and backflushing operations. The systems provide high speed separation and analysis of polar organic compounds with minimal sample loss, alteration or contamination attributable to the absence of valves in the sample flow path.

There are presently available gas chromatography systems used in industry for the separation of polar compounds which utilize a tandem combination of polar and non-polar analytical columns. The present practices are exemplified by ASTM procedure designation D 4815-89 which establishes a standard test method for evaluating certain alcohols and methyl tertiary butyl ether (MTBE) and gasoline by gas chromatography. In accordance with that procedure, however, a mechanical valve is implemented in the sample flow path which is used to direct the flow of sample and vent components which are not of interest. The device and the procedure established by the ASTM methodology possess a number of significant shortcomings. Of principal concern is the fact that by incorporating a mechanical valve in the sample flow stream, system dead volume is increased and the contamination of the sample by the valve is a constant concern. In addition, the detection limits of this system are extremely limited as well as its operational speed and flexibility. The gas chromatography systems in accordance with this invention provide significant improvements in undertaking this type of separation procedure.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE INVENTION

Figure 1:
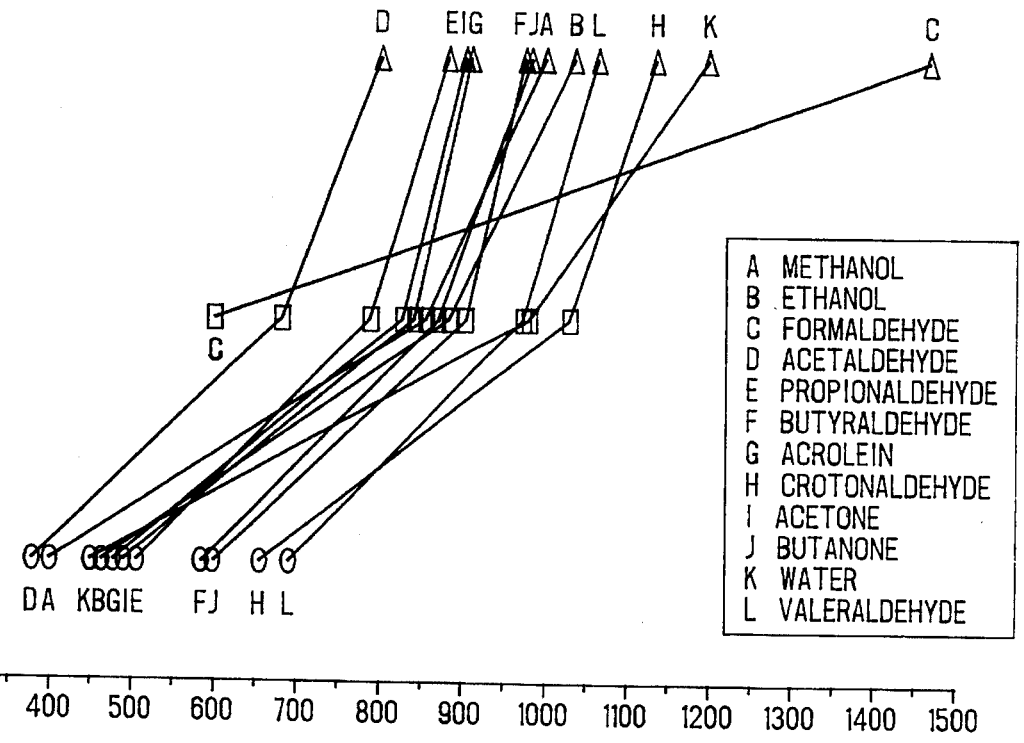
FIG. 1 is a chart showing the relative retention of a number of polar compounds of interest related to three example stationary phase materials used in a gas chromatography analytical column.

The concept of a group separation of polar from non-polar compounds implemented by this invention is illustrated in FIG. 1, where retention index values are plotted for some polar oxygen containing compounds including water on three stationary phase materials for an analytical column; a very polar phase (Carbowax 300) designated by triangles in the top row, a moderately polar phase (Carbowax 20M) designated by squares in the middle row, and a non-polar phase (SE-30) designated by ellipses in the bottom row. The compounds listed in FIG. 1 are considered target polar compounds which the gas chromatography systems of this invention specifically seek to evaluate. The retention index compares the retention characteristics of a compound to that of non-polar normal alkanes, which are assigned values of 100 times the number of carbon atoms in the alkane. For example, a compound that elutes between n-pentane (retention index equals 500) and n-hexane (retention index equals 600) will have a retention index value between 500 and 600. Note how the retention index values for the polar compounds are shifted to much greater values on the polar separation columns (top and middle rows). Notice also that the elution orders are switched for some of the target compounds as the stationary phase material is changed. In this invention the concept of combining segments of columns of different polarities is used to obtain selectivity control in the final separation. In this specification, reference to a "polar" column refers to the greater solubility of polar molecules in its stationary phase resulting in a greater retention or retardation of polar molecules. Similarly, a "non-polar" column preferentially delays non-polar compounds.

Four groups of compounds present in many environmental, process stream and laboratory samples can be identified and considered in developing a separation strategy for polar organic compounds. These groups are the target polar compounds, so-called permanent gases, non-polar hydrocarbon compounds, and water vapor. The target polar compounds usually contain atoms in addition to carbon and hydrogen which can interact strongly with certain polar stationary phases used for gas chromatography. These polar compounds of interest include each of the compounds listed in FIG. 1 and can be more broadly defined to include aldehydes, ketones, alcohols and chlorinated hydrocarbons. Another group of constituents of a sample are non-polar hydrocarbon molecules. Such non-polar molecules usually contain only carbon and hydrogen, however, some compounds which contain only carbon and hydrogen are also quite polar and typically contain aromatic rings. Another group of constituents of a sample mixture are so-called permanent gases, these includes CO, $CO_2$, $N_2O$, NO and $NO_2$ and also methane ($CH_4$) (since it is very difficult to trap using conventional GC methodologies).

This invention uses a series combination of a very polar column and a non-polar column to separate the target compounds from other, less polar compounds and permanent gases in the sample. Note that all the target compounds in FIG. 1 have retention index values greater than 800 on the very polar phase (top row), and values less than 700 on the non-polar phase (bottom row).

Figure 2:
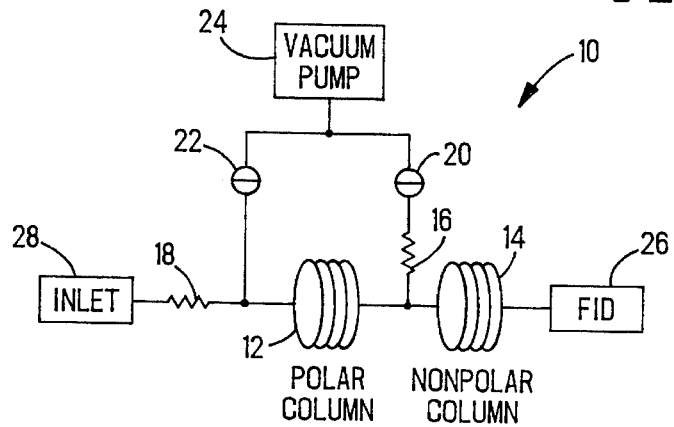
FIG. 2 is a pictorial representation of a gas chromatography system in accordance with a first embodiment of this invention.

Now with reference to FIG. 2 a first embodiment of a GC system of this invention is illustrated and is generally designated there by reference number 10. Gas chromatography system 10 includes a first polar analytical column 12 connected in series fashion to a second non-polar column 14. Lines shown in FIG. 2 (as well as FIG. 3) denote fluid flow conduits. Pneumatic restrictors 16 and 18 are provided in the conduits which are preferably comprised of a length of small diameter fused silica capillary tubing and are employed to provide appropriate flow rate and pressure balancing to provide the desired fluid flow behaviors. Fluid valves 20 and 22 are preferably pneumatically controlled gas valves which are shown in FIG. 2 in a closed position. Vacuum pump 24 is connected as shown in the figure and acts as a vent for the system. A detector 26 is connected to the output end of non-polar column 14 and may take various forms. A flame ionization detector (FID) 26 is shown in FIG. 2. GC system 10 provides a first conduit circuit through both columns 12 and 14 and FID 26, a second conduit circuit communicating vacuum pump 24 to the first circuit between the columns, and a third conduit circuit communicating the vacuum pump to the first conduit circuit before column 12.

Inlet system 28 is shown in diagrammatic fashion only in FIG. 2. Inlet system 28 could take various forms such as cryo-focusing systems utilizing bare metal tubes or porous layer open tubular (PLOT) configuration trap tubes which are placed in a controlled temperature environment to either trap components at a low temperature and elute them when a heating electrical pulse passes through the trap tube elements. Examples of such inlet systems are described in issued U.S. Pat. Nos. 5,096,471; 5,141,534; 5,205,845; 5,141,532; and 5,288,310, which are hereby incorporated by reference. Any inlet system capable of providing a narrow sample plug could be used in connection with this invention (i.e. a concentrated accumulation of a sample introduced into the GC system over a short duration time period). Inlet system 28 is assumed to further act as a point of introduction of a carrier gas, in accordance with conventional GC system designs.

In operation, a sample mixture is injected into GC system 10 via inlet system 28. It is assumed that the sample mixture would be comprised of compounds which can be organized in the previously described four distinct groups. In the initial phase of operation of GC system 10, valve 20 is open whereas valve 22 remains closed. Analysis is begun by injecting a sample plug onto polar column 12. Polar column 12 has a high degree of interaction with the polar target compounds; low boiling point non-polar compounds and permanent gases travel quickly through the polar column and are vented through restrictor 16, valve 20 and vacuum pump 24.

Note that after separation on the polar column, it will be possible to vent non-polar compounds with retention index values less than 700 (compounds more volatile that n-heptane) while still retaining all the target compounds. Permanent gases also will be vented during this step. Note that a reverse gas flow through the non-polar column 14 (backflush flow) prevents any sample components from reaching the non-polar column during this phase of operation. Also note that the pressure at the connecting point between polar column 12 and non-polar column 14 may be less than one atmosphere, depending on the pressure drop encountered through restrictor 16. The use of reduced outlet pressure at FID 26 (vacuum outlet GC) can result in improved resolution, particularly for short and/or wide bore capillary columns. Alternatively, the low boiling point non-polar organic compounds can be vented to atmospheric pressure by removing restrictor 16 and opening valve 20 to the atmosphere rather than to the vacuum pump. The venting operation is continued until just before the first target compound elutes from polar column 12. For the example shown in FIG. 2, the venting operation continues until compounds with retention index values of about 700 elute from polar column 12.

When venting of the permanent gases and low boiling point non-polar compound is complete, the target polar compounds and higher boiling point non-polar compounds which may have similar retention times on polar column 12 are transferred to non-polar column 14 by closing valve 20. Positive pressure applied by inlet system 28 drives the flow. In the non-polar column 14 non-polar compounds are retarded relative to any retained polar compounds upon elution the polar components are detected at FID 26. The results is that the target polar compounds can be detected with minimal interference from the later eluting non-polar compounds.

The temperature of non-polar column 14 is adjusted to give adequate separation of the polar target compounds while more strongly retaining the non-polar compounds which co-elute with the polar compounds from polar column 12. For the example shown in FIG. 1, the target compounds will then elute from the non-polar column with retention index values less than 700. However, most non-polar compounds that would normally elute in this range will have been vented.

After detection of the last of the target compounds, valve 22 is opened and both columns 12 and 14 are rapidly backflushed through vacuum pump 24. Pneumatic restrictors 16 and 18 shown in FIG. 2 are used to control the gas flow during the various parts of the column cycle time.

Figure 3:
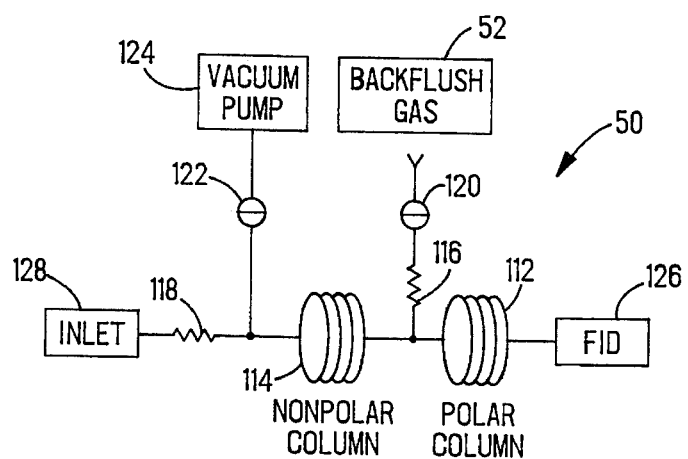
FIG. 3 is a pictorial representation of a gas chromatography device in accordance with a second embodiment of this invention.

A second embodiment of this invention is illustrated in FIG. 3 and is generally designated there by reference number 50. Components having similar characteristics and functions as those described in connection with FIG. 2 are identified by like reference numbers in FIG. 3 with 100 added. The elements of gas chromatography system 50 are however, inter-connected in a different manner as indicated by the solid lines denoting fluid flow conduits in FIG. 3. A source of backflush gas 52 is provided through valve 120. A significant modification of the system shown in FIG. 3 is a reversal in the order of the series connected analytical columns. In GC system 50, non-polar column 114 precedes polar column 112. GC system 50 forms a first conduit circuit means through pneumatic restrictor 118 then through both columns 114 and 112, and FID 126, a second conduit circuit communicating backflush gas source 52 through valve 120 and pneumatic restrictor 116 to the first circuit between the columns, and a third conduit circuit communicating vacuum pump 124 through valve 122 to the first circuit just before column 114.

In GC system 50, non-polar column 114 is used to separate the permanent gases and low boiling point non-polar compounds and the higher boiling point non-polar compounds from the polar target compounds and some co-eluting higher boiling point non-polar compounds. No venting is needed since the permanent gases and low boiling point non-polar compounds will be essentially unretained on either column and thus are quickly vented through detector 126 at the outlet of polar column 112. Operation begins when a sample is injected into the system by inlet system 128 while both valves 120 and 122 are closed. After the target polar compounds and the co-eluting non-polar compounds are transferred from non-polar column 114 to polar column 112, the non-polar column is backflushed removing all higher boiling point compounds by opening valves 120 and 122. While column 114 is being backflushed, separation is continued in polar column 112. The target polar compounds are more strongly retained by polar column 112 and thus elute after the non-polar compounds which co-elute with the target compounds from non-polar column 114. Since the last components to elute from the polar compound are the target polar compounds, no backflush of polar column 112 is required.

As a modification of GC system 50, the vacuum pump 124 may be eliminated and the backflushing of non-polar column 114 can be through valve 122 to atmospheric pressure. However, in such a system, backflush time will be greater as compared with systems using a vacuum pump.

While the above description constitutes the preferred embodiments of the present invention, it will be appreciated that the invention is susceptible of modification, variation and change without departing from the proper scope and fair meaning of the accompanying claims.

I claim:

1. A gas chromatography system for the separation and analysis of polar compounds of interest from a sample containing both polar compounds and non-polar compounds, comprising:

an inlet system for injection of said sample, a first analytical separation column having a polar stationary phase material which retards at least some of said polar compounds relative to at least some of said non-polar compounds, a second analytical separation column having a non-polar stationary phase material which retards at least some of said non-polar compounds relative to said polar compounds of interest, a detector for providing an output in response to the elution of said polar compounds and said non-polar compounds of said sample, vent means for venting fluids, first conduit circuit means for defining a fluid flow path from said inlet system first into said first column, into said second column and thereafter to said detector, second conduit circuit means for defining a fluid flow path from said first conduit circuit means between said first and second columns and said vent means, and valve means placed in said second conduit circuit means for controlling the flow of fluids through said first conduit circuit means wherein upon injection of said sample by said inlet system said polar compounds of interest are retarded on said first column relative to at least some portion of said non-polar compounds, and wherein said portion of said non-polar compounds are vented through said second conduit circuit means and said vent means and upon elution of said polar compounds of interest from said first column, causing said polar compounds of interest to pass into said second column and thereafter said polar compounds of interest are evaluated by said detector.

2. A gas chromatography system according to claim 1 wherein said vent means comprises a vacuum pump.

3. A gas chromatography system according to claim 1 wherein said sample includes one or more compounds from the group including aldehydes, ketones, alcohols and chlorinated hydrocarbons.

4. A gas chromatography system according to claim 1 wherein said polar compounds of interest exhibiting a retention index value of greater than 700 on said first column, where the retention index value indicates retention of said sample compounds relative to non-polar alkanes, which are assigned index values of 100 times the number of carbon atoms in the alkane and wherein said compounds vented by said vent means exhibit a retention index value of less than about 700 with respect to said first column.

5. A gas chromatography system according to claim 1 further comprising a third conduit circuit means for defining a fluid flow path from said first conduit circuit means between said inlet system and said first column, and said vent means for backflushing said columns, and second valve means in said third conduit circuit means for controlling the flow of fluids through said third conduit means.

6. A gas chromatography system for the separation and analysis of polar compounds of interest from a sample containing both polar and non-polar compounds, comprising:

an inlet system for injection of said sample, a first analytical separation column having a non-polar stationary phase material which retards at least some of said non-polar compounds relative to said polar compounds of interest, a second analytical separation column having a polar stationary phase material which retards said polar compounds of interest relative to at least some of said non-polar compounds, a detector for providing an output in response to the elution of said polar compounds and said non-polar compounds, a source of carrier gas, first conduit circuit means for defining a fluid flow path from said inlet system first into said first column, into said second column and thereafter to said detector, second conduit circuit means for defining a fluid flow path from said first conduit circuit means between said first and second columns and said source of carrier gas, and valve means placed in said second conduit circuit means for controlling the admission of said carrier gas from said source of carrier gas into said first conduit circuit means thereby controlling the flow of fluids through said first conduit circuit means wherein upon injection of said sample by said inlet system, at least some portion of said non-polar compounds are retarded on said first column relative to said polar compounds of interest, and wherein upon elution of said polar compounds of interest from said first column said polar compounds of interest pass into said second column and thereafter said polar compounds of interest are evaluated by said detector and wherein upon said polar compounds of interest passing into said second column, said valve means opening to admit said carrier gas into said first conduit circuit means thereby backflushing said first column.

7. A gas chromatography system according to claim 6 wherein said sample includes one or more compounds from the group including aldehydes, ketones, alcohols and chlorinated hydrocarbons.

8. A gas chromatography system according to claim 6 wherein said sample includes said polar compounds of interest exhibiting a retention index value of greater than 700 on said second column, where the retention index value indicates retention of said polar compounds of interest relative to non-polar alkanes, which are assigned index values of 100 times the number of carbon atoms in the alkane.

9. A gas chromatography system according to claim 6 further comprising a vent means and a third conduit circuit means for defining a fluid flow path from said first conduit circuit means between said inlet system and said first column and said vent means for backflushing said columns and second valve means in said third conduit circuit means for controlling the flow of fluids through said third conduit circuit means.

10. A gas chromatography system according to claim 9 wherein said vent means comprises a vacuum pump.

11. A gas chromatography system for the separation and analysis of polar compounds of interest from a sample containing both polar and non-polar compounds, comprising:

an inlet system for injection of said sample, a polar analytical separation column having a polar stationary phase material which retards said polar compounds of interest relative to at least some of said non-polar compounds, a non-polar analytical separation column having a non-polar stationary phase material which retards at least some of said non-polar compounds relative to said polar compounds of interest, a detector for providing an output in response to the elution of said polar compounds and said non-polar compounds of said sample, first conduit circuit means for defining a series flow path from said inlet system through said polar and non-polar columns in either order and thereafter to said detector, second conduit circuit means for defining a flow path from said first conduit circuit means between said polar and non-polar columns, valve means placed in said second conduit circuit means for controlling the flow of fluids through said second conduit circuit means wherein upon injection of said sample by said inlet system said valve means is actuated to prevent at least some of said non-polar compounds from passing through said detector while permitting said polar compounds of interest to pass through said detector.

12. A gas chromatography system according to claim 11 wherein said columns are placed to cause said sample to first flow into said polar column and thereafter into said non-polar column.

13. A gas chromatography system according to claim 12 further comprising a vent means and a third conduit circuit means for defining a fluid flow path from said first conduit circuit means between said inlet system and said first column and said vent means for backflushing said columns and second valve means in said third conduit circuit means for controlling the flow of fluids through said third conduit circuit means.

14. A gas chromatography system according to claim 11 wherein said columns are placed to cause said sample to first flow into said non-polar column and thereafter into said polar column.

15. A gas chromatography system according to claim 14 further comprising a source of carrier gas communicating with said second conduit circuit means and said valve means actuated to allow said carrier gas to backflush said non-polar column when said polar compounds of interest passes into said polar column.

16. A gas chromatography system according to claim 11 wherein said sample includes one or more compounds from the group including aldehydes, ketones, alcohols and chlorinated hydrocarbons.

17. A gas chromatography system according to claim 11 wherein said sample includes compounds exhibiting a retention index value of greater than 700 on said polar column, where the retention index value indicates retention of said sample compounds relative to non-polar alkanes, which are assigned index value of 100 times the number of carbon atoms in the alkane.

* * * * *

UNITED STATES PATENT AND TRADEMARK OFFICE
CERTIFICATE OF CORRECTION

PATENT NO. : 5,498,279
DATED : March 12, 1996
INVENTOR(S) : Mark A. Klemp

It is certified that error appears in the above-indentified patent and that said Letters Patent is hereby corrected as shown below:

Column 10, line 4, claim 17, after "index" delete "value" and insert ---values---.

Column 8, line 66, claim 15, after "interest" delete "passes" and insert ---pass---.

Signed and Sealed this

Thirteenth Day of August, 1996

*Attest:*

BRUCE LEHMAN

*Attesting Officer*    Commissioner of Patents and Trademarks